United States Patent
Carr et al.

(10) Patent No.: US 8,696,567 B2
(45) Date of Patent: Apr. 15, 2014

(54) ASSAY FOR POSITIONING A FEEDING TUBE AND METHOD THEREOF

(75) Inventors: Reuben Carr, Edinburgh (GB); Lucy Farley, Newton St. Cyres (GB)

(73) Assignee: Ingenza Ltd., Midlothian (GB)

(*) Notice: Subject to any disclaimer, the term of this patent is extended or adjusted under 35 U.S.C. 154(b) by 138 days.

(21) Appl. No.: 12/958,117

(22) Filed: Dec. 1, 2010

(65) Prior Publication Data

US 2011/0270054 A1 Nov. 3, 2011

Related U.S. Application Data

(60) Provisional application No. 61/283,401, filed on Dec. 3, 2009.

(51) Int. Cl.
| | |
|---|---|
| *A61B 5/00* | (2006.01) |
| *C12Q 1/34* | (2006.01) |
| *C12Q 1/25* | (2006.01) |
| *C12Q 1/44* | (2006.01) |
| *G01N 33/48* | (2006.01) |
| *A61B 10/00* | (2006.01) |

(52) U.S. Cl.
CPC .. *C12Q 1/34* (2013.01); *C12Q 1/25* (2013.01); *C12Q 1/44* (2013.01); *G01N 33/48* (2013.01); *A61B 2010/0061* (2013.01); *A61B 5/68* (2013.01); *A61B 5/6846* (2013.01)
USPC ............ 600/300; 600/361; 600/309; 435/7.1; 435/7.4; 435/18; 435/19

(58) Field of Classification Search
None
See application file for complete search history.

(56) References Cited

U.S. PATENT DOCUMENTS

| | | | |
|---|---|---|---|
| 5,028,533 A | 7/1991 | Tubb | |
| 5,891,054 A | 4/1999 | Metheny et al. | |
| 6,511,814 B1* | 1/2003 | Carpenter | 435/7.21 |
| 2005/0070005 A1 | 3/2005 | Keller | |
| 2006/0003394 A1* | 1/2006 | Song | 435/7.92 |
| 2008/0004598 A1 | 1/2008 | Gilbert | |
| 2008/0063566 A1* | 3/2008 | Matsumoto et al. | 422/68.1 |
| 2008/0146896 A1 | 6/2008 | Rabinowitz et al. | |
| 2008/0233615 A1 | 9/2008 | Klaenhammer et al. | |

(Continued)

FOREIGN PATENT DOCUMENTS

| | | |
|---|---|---|
| EP | 0160467 A2 * | 6/1985 |
| WO | WO 2009024805 A1 * | 2/2009 |

OTHER PUBLICATIONS

Gharpure, V. et al. "Indicators of postpyloric feeding tube placement in children"; Crit Care Med: Pediatric Critical Care, vol. 28; No. 8; 2000; p. 2962-2966.*

(Continued)

*Primary Examiner* — Bill Thomson
*Assistant Examiner* — Marie Archer
(74) *Attorney, Agent, or Firm* — McDermott Will & Emery LLP; Avani C. Macaluso (57) ABSTRACT

The present invention discloses a bedside or point of care assay for properly positioning a feeding tube in the stomach of a patient based on detecting the presence of a hydrolytic enzyme found in the stomach by an ester substrate which can be impregnated on a pH strip. The application of this test reduces the risk of tube misplacement and the resulting harm to the patient that occurs in the event of tube misplacement.

11 Claims, 7 Drawing Sheets
(3 of 7 Drawing Sheet(s) Filed in Color)

(56) References Cited

U.S. PATENT DOCUMENTS

| | | |
|---|---|---|
| 2008/0269706 A1 | 10/2008 | Long et al. |
| 2009/0134869 A1* | 5/2009 | Lee .................... 324/309 |
| 2009/0248450 A1 | 10/2009 | Fernandez |
| 2010/0028916 A1* | 2/2010 | Ambar et al. ........... 435/7.72 |

OTHER PUBLICATIONS

Farath, S. et al "Pepsin, a Reliable Marker of Gastric Aspiration, IsFrequently Detected in Tracheal Aspirates From Premature Ventilated Neonates: Relationship With Feeding and Methylxanthine Therapy"; Journal of Pediatric Gastroenterology and Nutrition; 43:336-341, Sep. 2006.*

Metheny, N. A. et al. "Assessing Placement of Feeding Tubes"; The American Journal of Nursing, vol. 101, No. 5 (May 2001), pp. 36-46.*

Metheny, N. A. "Preventing Respiratory Complications of Tube Feedings: Evidence-Based Practice"; Am J Crit Care 2006;15:360-369.*

Hamosh, M. et al. "Fat digestion in the newborn"; J. Clin. Invest.; vol. 7., Mar. 1981; 838-846.*

Richardson, D. S. "An Evidence-Based Approach to Nasogastric Tube Management: Special Considerations"; Journal of Pediatric Nursing, vol. 21, No. 5 (Oct.), 2006, p. 388-393.*

Gupta, R. et al. "Lipase assays for conventional and molecular screening: an overview", Biotechnol. Appl. Biochem. (2003) 37, 63-71.*

Tietz, N. W. et al. "Proposed Standard Method for measuring Lipase Activity in Serum by a Continuous Sampling Technique"; Clin. Chem. 19/11, 168-1275 (1973).*

Tietz, N. W. et al. "Lipase Activity Measured in Serum by a Continuous-Monitoring pH-Stat Technique-an Update"; Clin. Chem. 35/8, 1688-1693 (1989).*

Metheny, N. et al; "pH and concentrations of Pepsin and Trypsin in feeding tube aspirates as predictors of tube placement"; (1997); Journal of Parenteral and Enteral Nutrition, vol. 21, No. 5, p. 279-285.*

Metheny, N. et al; "Monitoring feeding tube Placement"; (Oct. 2004); Nutrition in Clinical Practice; 19:487-495.*

Westhus, N.; "Methods to test feeding tube"; (Sep./Oct. 2004); MCN the American Journal of Maternal Child Nursing; vol. 29, No. 5; p. 282-287.*

\* cited by examiner

Phenol red – pH indicator below pH 6.8   above pH 8.2

| Position | Tributyrin | Lipase |
|---|---|---|
| Top right | - | - |
| Top left | + | - |
| Bottom right | - | + |
| Bottom left | + | + |

ASSAY FOR POSITIONING A FEEDING TUBE AND METHOD THEREOF

CROSS-REFERENCE TO RELATED APPLICATION

The present application claims priority to and the benefit of U.S. Provisional Application No. 61/283,401 filed on Dec. 3, 2009, and is incorporated by reference and made a part hereof.

BACKGROUND OF THE INVENTION

1. Field of the Invention

The present invention is generally related to the field of medical diagnostics for verifying the location of a medical device in a patient. More particularly, the present invention relates to the use of an indicator substance which is acted upon, either directly or indirectly, by an enzyme specifically formed or located at the place where the medical device should be positioned. Specifically, the present invention discloses a point of care method and assay for accurately positioning a feeding tube in the stomach of a patient based on detecting the presence of a hydrolase enzyme found in the stomach where the feeding tube should be positioned.

2. Description of the Prior Art

Feeding tubes are medical devices that primarily provide patients with proper nourishment or medication to those who are unable to ingest food or drugs on their own. There are numerous types of feeding tubes available depending on the method of insertion. For example, nasogastric tubes (NG tubes) are inserted through the nose, past the throat, and down into the stomach of patients, whereas orogastric tubes (OG tubes) are inserted through the mouth, past the throat and into the stomach. Gastric tubes (G-tubes) or percutaneous endoscopic gastronomy tubes (PEG tubes) are also available and are inserted into the abdomen via a small incision into the stomach. G-tubes are commonly used for long-term enteral nutrition. Feeding tubes have other uses besides providing nourishment, in that they can also be used to empty and decompress the stomach during surgery. The type of feeding tube desired will vary based on a patient's age and medical condition. The fitting and use of feeding tubes are considered common medical procedures with widespread use. In fact sales figures from the top three nasogastric tube manufacturers estimate that 1.5 billion tubes were sold in 1999 (Hoffman, S. et al., Langenbeck's Arch Surg, 386:402-409 (2001)). Regardless of the method of insertion it is important that feeding tubes are accurately positioned in the stomach of patients.

The positive identification of the placement of a feeding tube in a patient during and after insertion is highly desirable to a high degree of precision and accuracy. Incorrect placement of a feeding tube and subsequent administration of food or drugs can have serious or life threatening consequences for the patient. To ensure safe positioning of feeding tubes during clinical procedures, the distal end of the feeding tube must be positioned within the stomach and not in other locations within the body. Failure to locate the feeding tube in the stomach can result in harm and even death to the patient, particularly if feeding occurs into the lungs. Once a feeding tube is fitted into a patient, frequent placement checks are required to be carried out by a clinician to ensure correct feeding tube placement is maintained. Current recommended clinical guidance dictates that testing should be done before each feeding or when medication is administered, following vomiting, retching or coughing and if there is any indication that the tube displacement may have occurred, e.g., if the tape securing the tube is loose, if the tube is no longer visible or if it is kinked. The mean duration a patient has a nasogastric feeding tube fitted is 5.2 days (Park, R. H. R., BMJ, 304: 1406-9 (1992)) and the frequency of the testing should occur several times a day. Therefore, the total number of tests carried out to verify feeding tube placement is extremely high.

Several existing methods for verifying the placement of a feeding tube are known, including those relying on a sample obtained by aspiration (withdrawal of a liquid sample of a patient through the tube following placement). The tests of the sample obtained by aspiration include examining the visual characteristics of the aspirate, pH measurement, laboratory measurements of concentration levels of bilirubin, pepsin and trypsin, and measurement of the carbon dioxide level at the proximal end of the feeding tube. Other tests to confirm correct placement of a feeding tube, not requiring the sampling of liquid, include auscultating for a gurgling sound over the abdomen, measuring the length from the nose to the proximal end of the tube and X-ray examination.

There are conflicting opinions on the reliability, accuracy and precision of verification tests used to confirm feeding tube placement. The widely accepted 'gold standard' indication test is by X-ray examination. Although X-ray examination has an excellent success rate, in practice this verification test is not routinely used for every placement check, as a result of the prohibitive cost, impracticality and harm to the patient due to the quantity and frequency by which confirmation tests are recommended to occur. Use of X-ray examination to determine feeding tube placement results in longer periods between feedings, overexposure to X-rays and general discomfort associated with X-ray examinations. During the time delay between X-ray examination and feeding, should tube movement occur, the test is invalidated and the X-ray examination must be repeated. Occasionally even the X-ray test can be misinterpreted if the image is not interpreted correctly by a properly trained professional or if the image is complicated by the status of the patient thus making the identification of the tube or its location less certain. All these factors are detrimental to patient health. In many instances the use of an X-ray examination to carry out this test is simply unavailable outside of hospitals or larger institutions which can offer this service.

Laboratory testing of bilirubin, pepsin and trypsin concentration levels can be a useful indicator to predict feeding tube location, but such methods are not practical for clinical use, particularly for a bedside or point of care setting (Metheny, N. et al., J Parenter Enteral Nutr, 21: 279 (1997)). The implementation of tests involving measuring concentration levels of bilirubin, pepsin and trypsin have not been pursued because of the high number of samples requiring analysis, the requirement for rapid delivery and turnaround of results, the provision of a suitable laboratory facility within close proximity to the patient, the overwhelming volume of testing required and the cost burden that would be incurred to deliver this service. A simple reliable point of care or bedside test is needed to determine accurate placement of a feeding tube in a patient's stomach. In fact, the Department of Health in the United Kingdom has recognized the need to improve bedside testing methods that do not rely on x-ray techniques and is hopeful that in the future such a test will become possible. (www.haps.bham.ac.uk/publichealth/psrp/documents/PS048_Call_for_proposals_NG_tubes.pdf)

In the absence of a suitably rapid, low cost, convenient, unambiguous and accurate test within a bedside or point of care clinical setting, less accurate methods are sometimes used auscultating for a gurgling sound over the abdomen or visual inspection of the aspirate. These practices involve either combination or multiple testing, such as those outlined above, to try to offset the high risks attributable to the person doing the test based on their clinical experience. Such practices are recognized as problematic and detailed protocols are described to avoid possible complications (http://www.nrls.npsa.nhs.uk/resources/?EntryId45=59794 and Yardley, I. et al., Clinical Medicine, Journal of the Royal College of Physicians, Vol. 10, No. 3: pp. 228-230(2010)).

Another commonly used test to verify correct feeding tube placement is measuring the pH of an aspirate sample from where the feeding tube is placed. The pH of stomach aspirate is generally expected to be lower (more acidic) than aspirate from an incorrectly located feeding tube (e.g., the lungs) due to the presence of gastric acid in the stomach. The reliability provided by a pH test in determining successful placement of the feeding tube is higher than comparable methods available within a clinical bedside environment. But even with this method, there are many instances where this test is unsuitable. This is especially so for those patients whose gastric pH is raised from normal levels by the use of common prescription drugs and medication. Additionally, the normal level of gastric pH is known to vary widely between individuals, depending on several external factors. The pH of the stomach will even vary depending upon the time since the patient's last meal. pH tests are administered by clinical staff using indicator paper. Since the range for gastric aspirate is typically between pH 0 and pH 7 it can make accurate diagnosis difficult and unreliable, owing to the differences in color of the indicator paper across this range. This color differentiation, and hence pH estimation, can also be influenced by external factors such as ambient light and the eyesight of the clinician making the assessment.

Figure 7:
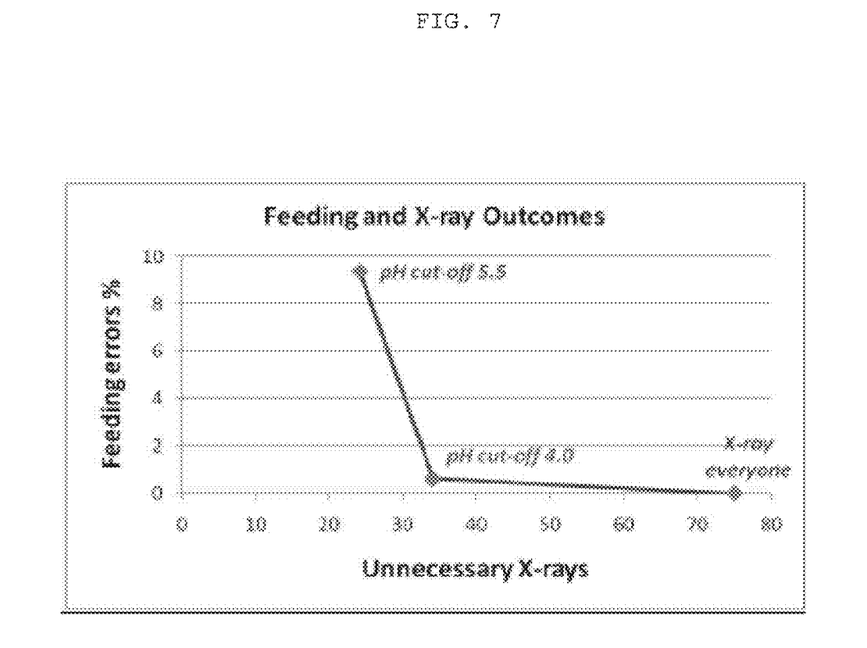
FIG. 7 is a graphical representation of the feeding tube verification guidelines and errors.

Detailed assessments by the Department of Health have been made as to what is a safe acidic pH "cut off" measurement to ensure the tube is correctly positioned within the stomach. In the past litmus paper has been used, but use of the litmus test has recently been criticized for being inaccurate and therefore pH indicator paper should be used in its place. As depicted in Table 1 and FIG. 7, a pH measurement of 4.0 or less results in correct tube placement, but the overall failure rate of the placement tests increases, necessitating additional X-ray tests. Elevating the pH measurement "cut off" to 5.5 enables more tests to indicate stomach placement, thus improving the "pass rate" but with an increased risk that correct location may not be made. Therefore a lower pH "cutoff" (e.g. pH 4.0) is preferable to ensure the best possible patient safety by accurately determining stomach placement, albeit with an increased burden on X-ray use. A preferable option is therefore to use the lower pH cutoff (pH 4.0) but with a test that achieves a high "pass rate", thereby maintaining patient safety and reducing or avoiding an increase in X-ray confirmation tests.

TABLE 1

Outcomes of Clinical Guidelines

|  | Placement Errors | Unnecessary X-ray |
|---|---|---|
| pH 5.5 feed; X-ray everyone with pH > 5.5 | 9.38% | 24.15% |
| pH 4 feed; X-ray everyone with pH > 4 | 0.62% | 34.05% |
| X-ray everyone | 0 | 75% |

Currently, misplaced naso or orogastric tubes, not detected prior to use is a significant patient safety issue and was the second most reported preventable patient safety incident in a 2009-2010 United Kingdom National Health Service annual report. Such preventable safety incidents also referred to as "never events", can lead to hospitals losing important funding. It should be highlighted that the incidence of feeding tubes identified as being misplaced is infrequent. However, although the chance of misplacement is small, owing to the tremendous number of verification tests carried out each year (estimated to be many millions) the absolute number of misplacements is high. Accurate determination of the error rate of existing feeding tube misplacements is difficult to obtain since they are poorly reported and depend on how they are defined. In adults, tube misplacements range is thought to average at 4%, while in children the figure is higher, ranging somewhere between 21-43.5%. Based on the extremely high number of verification tests estimated to be carried out each year, it is clear that robust point of care tests to confirm feeding tube placement are imperative since even though feeding tube misplacement events occur at a low rate with the current usage, they still happen reasonably frequently.

In summary, the results of these practices expose patients fitted with a feeding tube to a high level of risk. The negative outcomes resulting from the misdiagnosis or lack of diagnosis of the feeding tube placement are dire, causing numerous instances of severe harm and death. Consequently, there is a critical need to address the requirements of a suitable simple point of care verification test. The requirements of such a verification test must include the following features: operation at the point of care of a patient, low cost, rapid result, low design complexity, minimal alteration to current practices, excellent reliability and no requirement for the user to comprehend the technical features underpinning the test.

The distal end of the feeding tube must be placed in the stomach and not the lung or the throat. Therefore, the identification of a species or entity which is uniquely present in the stomach and whose use incorporates the desirable features of the feeding tube verification test, as outlined above, is highly desirable. pH is one such indicator and is used in existing tests, but it is associated with a high degree of error and cannot be used in every circumstance. Since the primary physiological function of the stomach is digestion of food, the entities which facilitate digestion are likely to be present at a sufficiently high levels or degree of function or activity to provide sufficient sensitivity required for an improved feeding tube placement test. Those entities that are present exclusively in the stomach provide a route by which a point of care feeding tube placement test could become feasible. The main entities which carry out this digestive role in the stomach are hydrolase enzymes. These occur extensively throughout the stomach and are sub-classified into three main groups: proteases, glycoside hydrolases and lipases/esterases, depending on their mode of action and to which food group they act upon. The products resulting from these enzyme-catalysed chemical reactions offer an opportunity for a suitable detection method. For proteases the resulting products are smaller peptide fragments or amino acids, for glycoside hydrolases the products are smaller carbohydrate fragments or monosaccharides and for lipases/esterases the products are acids and alcohols. Detection of one or more of these products at the bedside using a test, featuring the desirable attributes outlined, would result in a highly desirable feeding tube placement diagnostic test. Critically, the exceptional selectivity associated with enzyme-catalyzed reactions would underpin the reliability and specificity of the test, in direct contrast to the ambiguous tests currently available. The present invention is provided to overcome limitations and drawbacks of the prior art and to provide novel aspects not heretofore available.

SUMMARY OF THE INVENTION

The present invention describes an improved medical diagnostic test which significantly lowers the current frequency of error for positioning of a feeding tube for administrating food or drugs in patients. The reduction in the frequency of error of tube placement significantly reduces the likelihood of severe harm or death to patients from feeding or drug delivery through an incorrectly positioned feeding tube in patients.

In one embodiment a method for accurately positioning a medical device in a patient is disclosed. The method comprises providing a medical device, obtaining a fluid sample from the area where the medical device is positioned and detecting the presence of an enzyme by an enzyme substrate as an indicator of accurate positioning of the medical device, where the enzyme is specifically found in the area of the body where the medical device should be positioned. The detection of the enzyme is conducted at the point of care of the patient.

In another embodiment, an assay is disclosed for accurately positioning a feeding tube in a stomach of a patient in which the assay includes impregnating an ester into pH paper for detecting the presence of a hydrolytic enzyme.

In yet another embodiment, a method for accurately positioning a feeding tube in a stomach of a patient is disclosed. The method requires providing a feeding tube and obtaining a body fluid sample from the area of the body where the feeding tube is positioned. The accurate positioning of the feeding tube is determined by detecting in the fluid sample the presence of a hydrolase enzyme based on an ester indicator using a point of care assay.

These and other aspects of the present invention will become apparent to those skilled in the art after a reading of the following description of the preferred embodiment when considered with the drawings, as they support the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The present invention is capable of embodiments in many different forms. Preferred embodiments of the invention are disclosed with the understanding that the present disclosure is to be considered as exemplifications of the principles of the invention and are not intended to limit the broad aspects of the invention to the embodiments illustrated.

The outlined shortcomings of current tests and the potentially advantageous features exhibited by hydrolase enzymes located in the stomach are the basis for the invention disclosed here. Human gastric lipase (HGL) is an enzyme which is formed and is located specifically within the stomach and not elsewhere in the body (See, Moreau et al., (Gastroenterology (1988)) 95: 1221-6, "Human Preduodenal Lipase Is Entirely of Gastric Fundic Origin"). This is a highly functional, selective and efficient hydrolase enzyme. The action of this enzyme on substrates containing an ester results in the release of a carboxylic acid and an alcohol product. The formation of the acidic product results in an overall net decrease in pH of the media in which the acidic product is released. Numerous modes of detection of pH are well known and several of these would be amenable to the practical limitations necessary for a point of care test.

In one embodiment, the present invention discloses impregnating a suitable ester compound in, on or within a pH indicating surface such that when the application of HGL occurs, acid is released and the observed pH change is registered by the associated indicator using pH paper or a pH meter. In another embodiment, the enzyme indicating output may be a current, an LCD, a voltage, or a handheld/portable measurement device. In order to determine the presence of a lipase, an aspirate sample is obtained from the patient where the feeding tube is positioned. Alternatively, an enzyme indicating substrate could be positioned on the distal end of the feeding tube to alleviate having to obtain an aspirate sample. The lowering of the pH in the presence of the enzyme substrate would give a clear and unequivocal confirmation of the presence of HGL by a decrease in pH, which would not occur in the absence of HGL or its substrate. This would effectively magnify the pH change already associated with the detection of gastric acid and since a hydrolase enzyme is a catalyst, the effect upon pH would be amplified greatly.

Owing to the exquisite degree of control and selectivity exhibited by lipase/esterases, the selection of a particularly suitable ester substrate can be made to enhance the test if necessary to improve selectivity and avoid false positive results. The ester is selected in such a way that only HGL, and not other non-gastric lipases/esterases, would efficiently hydrolyse the ester, thereby giving a greater degree of control, accuracy and reliability in the test. The selectivity differences in the way different lipases/esterases act on esters is widely reported. For example, the present invention discloses the use of esters including, but not limited to, tributyrin, tricaprylin, triacetine, n-butyric acid methyl, benzyl butyrate, ethyl levulinate, ethylacetate or tristerain.

A further feature of HGL is that the pH optimum of the enzyme is in the acidic pH range, so it can function efficiently within the normal acidic environment of the stomach. This property will allow a greater degree of control and selectivity to discriminate between HGL and non-gastric lipases/esterases, since fewer non-gastric lipases/esterases are able to tolerate and function within the acidic nature of the detection method described. Furthermore, since HGL operates optimally under acidic conditions, the change in pH is rapid so it is ideally suited for a bedside test. The formulation and preparation of the ester chemical within the pH indicating paper can also be selected to allow the most rapid and efficient reaction of the substrate to promote the release of the products. The formulation and preparation possibilities include, but are not limited to, homogenization and emulsification of the substrate. Further components can be included to enhance the assay by increasing the rate of the HGL reactions. Such components may include, but are not limited to, hormones such as gastrin or adjunctive agents known to accelerate the catalytic function of lipases/esterases.

The lowering of pH resulting from the release of acidic products by the specific action of HGL addresses the weaknesses associated with the existing pH indicating test, which is the currently preferred testing means used in a clinical setting. In this improved HGL specific test a genuine positive result arising from gastric acid (i.e. the low pH measurement of an aspirate) is unchanged from the conventional pH indicating test: the pH of the aspirate will be measured to be low. However, significantly in those test instances in which gastric pH is raised by the use of prescribed drugs or medical conditions, this HGL specific test would remove the greater degree of error present in those circumstances. Under those circumstances, using the current standard pH indicator paper test is ambiguous: the observed higher pH may be from a correctly placed feeding tube in the stomach of a patient with high stomach pH or it may be the result of an incorrectly located feeding tube. Consequently, the result is frequently misinterpreted or requires more costly follow-up action (e.g. X-ray) to determine feeding tube positioning.

Figure 1:
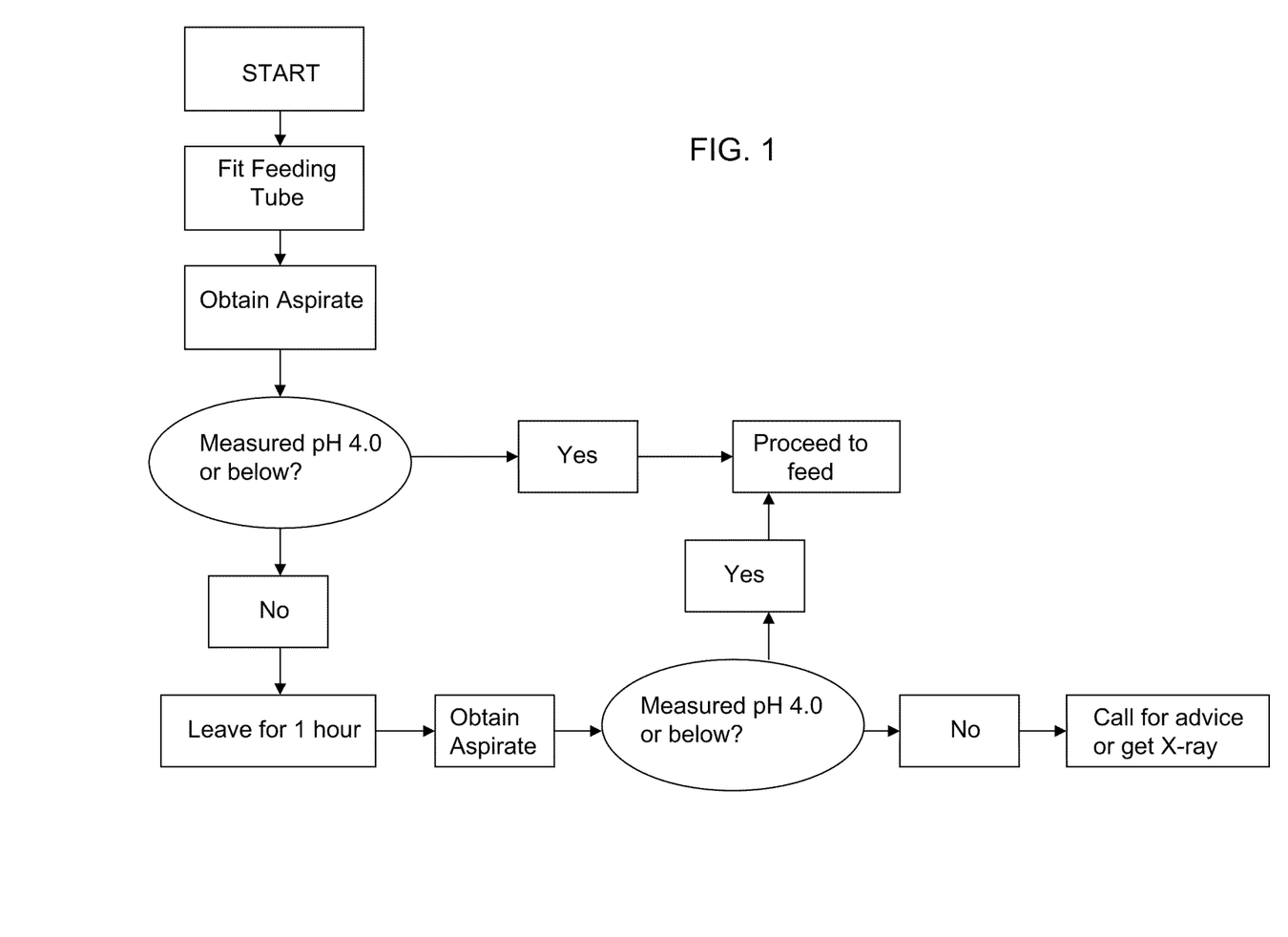
FIG. 1 is a flowchart of the decision making process of the present invention to confirm safe positioning of a feeding tube in a patient with pH indicating paper impregnated with an ester substrate.

With the present invention, the original high pH will rapidly drop, caused by the action of HGL on the impregnated ester resulting in a conclusive diagnostic pH paper colour change. Specifically, the pH will be less than the of a sample measured using a standard pH test without the presence of HGL. In those instances in which an aspirate sample was obtained but did not contain HGL, caused by incorrect feeding tube placement such as the lung and therefore not originating from the stomach, HGL would be absent and the pH would remain high and the diagnostic test would remain negative. The decision on whether to proceed to feeding can therefore be made with a much higher degree of confidence that the feeding tube is correctly positioned to avoid causing harm to the patient. The decision-making processes made by a clinician would be altered as a result (FIG. 1).

While the present invention specifically discloses detecting the presence of HGL using an ester substrate, other enzymes present specifically in the stomach can be detected using an appropriate substrate. For example, the presence of pepsin based on the substrate Azocoll could be used to generate a red colored product that can be detected at the bedside. Azo-dye is released by Azocoll digestion to generate a color product. Alternatively, the presence of a hydrolytic enzyme can be determined based on a colored or fluorescent product, and not on pH, where the product derives from an alcohol such as para-nitrophenol, umbelliferone, resorufin or dimedone yielding a specific colored or fluorescence response. For instance, glycoside hydrolases can be detected by the formation of a yellow colored product which is known for alpha-glucosidase action on 4-nitrophenyl-α-D-glucopyranoside which yields para-nitrophenol. Additionally, protease enzymes can be detected by a yellow colored product which is known for protease activity on peptides giving rise to the release of amino groups which readily react with trinitrobenzene sulfonic acid to form product adducts yielding a yellow color.

Pepsin is classified as a protease but also exhibits esterase activity (Nature, Vol. 204: p.580 (1964)). Therefore, pepsin detection utilizing its esterase behavior could be implemented as the basis for a bedside test using the same approach as outlined here with HGL. Alternative bedside detection can be based on coupling the hydrolase generated product to a secondary enzymatic process in order to generate a colored product, e.g., using oxidase or dehydrogenase enzymes. For example, monosaccharides as products generated by glycoside hydrolase action can be detected by coupling with glucose oxidase, amino acids as products generated by protease action can be detected by coupling with amino acid oxidase and alcohols generated by esterase action can be detected by coupling with alcohol oxidase. There are several methods available to assay the relevant oxidase or dehydrogenase and methods already exist that enable point of care tests to identify their activity (i.e., point of care blood glucose monitoring devices). Detection of each of these hydrolase enzymes utilizing the relevant coupled oxidase or dehydrogenase assay can enable a specific color forming product or change in redox (electrochemical) potential to be generated which enables a bedside detection of all the three main classes of hydrolase.

Additionally, the present invention further contemplates detecting the presence of enzymes that are found specifically in the area of the body where a medical device is to be positioned using a substrate indicator. For example, it is possible to determine the proper placement of a medical device in the duodenum or elsewhere in the digestive tract beyond the pyloric sphincter of a patient by determining the presence of digestive enzymes such as pancreatic lipases using a substrate indictor. The location of feeding tubes beyond the stomach, further down the digestive tract can be desirable depending of the requirements and needs of the patient.

The advantages of this HGL specific test overcome the shortcomings associated with the existing clinical indication tests used to confirm feeding tube placement. A greater frequency of conclusive testing results would be achieved and with a much higher degree of accurate testing when assessed alongside the existing verification testing methods. The reduction in the use of existing X-ray examinations to reach the same degree of confidence would offer additional benefits. These benefits include shorter periods of delayed feeding, reduced cost and greater reassurance that harm will not occur to patients during feeding. The use of X-ray examinations remains a viable means to confirm any ambiguous results from the proposed HGL test but these would be expected to be far fewer in number than currently observed.

The reliability of the test is noticeably improved for patients on medication which causes an increase in gastric pH. Where the stomach pH is low, the output of data, operation and results of the HGL-specific test is virtually unchanged, compared to the existing pH indication test in the example of a genuine positive result. The resolution and contrast of the pH indication would be generally improved since more acidic values result from (0-4) the HGL specific test and are much more readily distinguishable colors than pH values typically obtained using the existing indicating test ( 0-7), thereby reducing the risk of misdiagnosis. Current recommended guidelines for feeding tube placement by testing, as defined by agencies that advise clinicians on feeding tube placement checks, (e.g., National Patient Safety Agency in the National Health Service) can remain virtually unchanged. No technical insight or fundamental understanding is required beyond current levels of clinical competencies in order to carry out the disclosed test and interpret the results. The production cost to manufacture the HGL test is low. A significant reduction in the frequency of misdiagnosis of feeding tube placement for patients on medication or drugs which raise gastric pH has been demonstrated. Medical error is one of the top five causes of death in the western world. The HGL specific test will reduce the number of incidences of harm and deaths associated with misplaced feeding tubes.

EXAMPLE ONE

Figure 2:
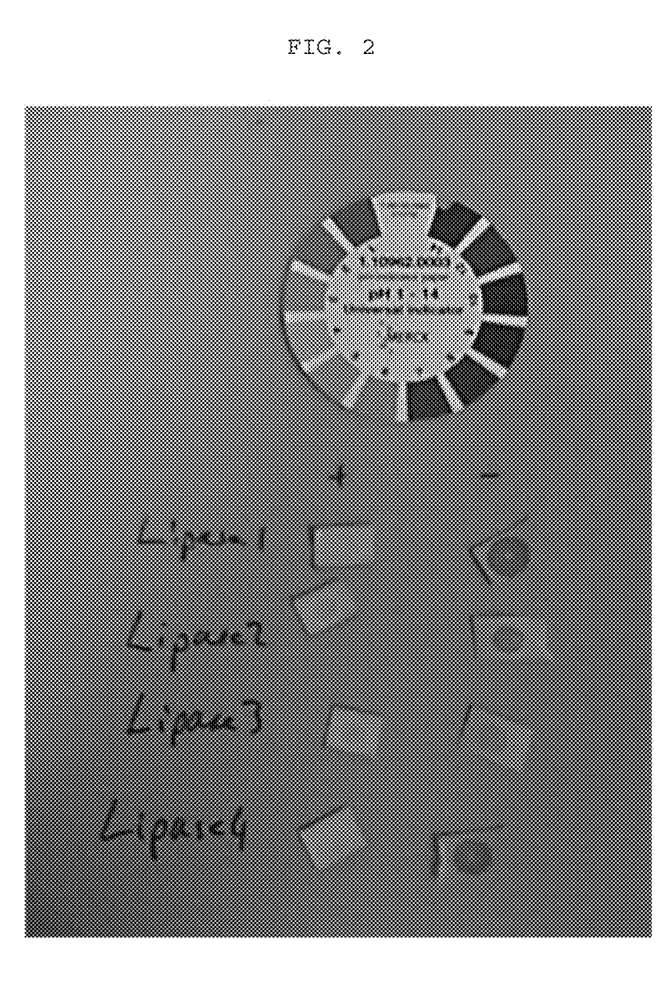
FIG. 2 is a photograph of the observed pH when four different commercial lipases are applied onto a universal pH indicator paper. Color change occurred and was completed with no further color change after 5 seconds. The left hand (+) column is pH strips impregnated with the ester tributyrin as described above. The right hand (−) column is the control test without substrate in the pH paper.

The assay of the present invention has an ester chemical impregnated into Ph indicator paper. The impregnation was carried out by adding 1 ml of tributyrin from Sigma to 9 ml of water, after which the mixture was vigorously shaken for 30 seconds to disperse tributyrin throughout the water in microdroplets. The pH indicator paper was immersed into the resulting mixture, removed and then dried to evaporate the residual water. Once dried, the prepared pH indicator paper containing tributyrin had a 20 microlitre drop applied which contained a dissolved lipase from Amano. Alongside this, a second pH indicator paper from the same source, but lacking the impregnated tributyrin had another 20 microlitre drop of the same dissolved lipase applied. After a short period the pH was examined using the reference pH indicator scale provided by the pH indicator paper manufacturer. The pH of the indicator paper containing the tributyrin was pH 4, while the control pH indicator measurement without tributyrin measured was close to pH 7. Three other lipases from different sources were also tested in the same manner and gave closely similar results demonstrating the significantly greater pH change when the ester is included. The results of these tests are shown in FIG. 2.

EXAMPLE TWO

It is well known in the art that the biochemistry and physiology between rabbit gastric lipase (RGL) and human gastric lipase (HGL) are similar. (See, Gargouri et al. (Biochimica et Biophysica Acta, 1006 (1989) 255-27, "Gastric lipases: biochemical and physiological studies.") Therefore, a sample containing lyphophilized rabbit stomach extracts (JO4001) were obtained after soaking stomachs in an appropriate buffer. The procedure corresponds to the first step of gastric lipase purification as reported in Carriere et al. (Eur. J. Biochem. (1991) 202:75-83). "Purification and biochemical characterization of dog gastric lipase.")

Lipase activity was measured at 5.5 using the pH-stat technique and tributyrin as substrate (See, Enzymology at Interfaces and Physiology of Lipolysis, "Standard assay of gastric lipase using pHstat and tributyrin as substrate") according to Moreau et al., Biochem Biophys Ascta. 960: 286-93 (1988). "Purification, characterization and kinetic properties of the rabbit gastric lipase."). The powder contains 66.3 lipase unit (U) per mg of powder, i.e. 6.63% w/w rabbit gastric lipase (RGL) based on the specific activity of purified RGL (1000 U/mg) under the same assay conditions. 1 U=1 mole of butyric acid release per minute. The flask contains 1 gram of JO-4001, i.e. 66.3 mg RGL. It is noteworthy that pepsin is also present in JO4001, but its concentration is not well characterized.

Figure 3:
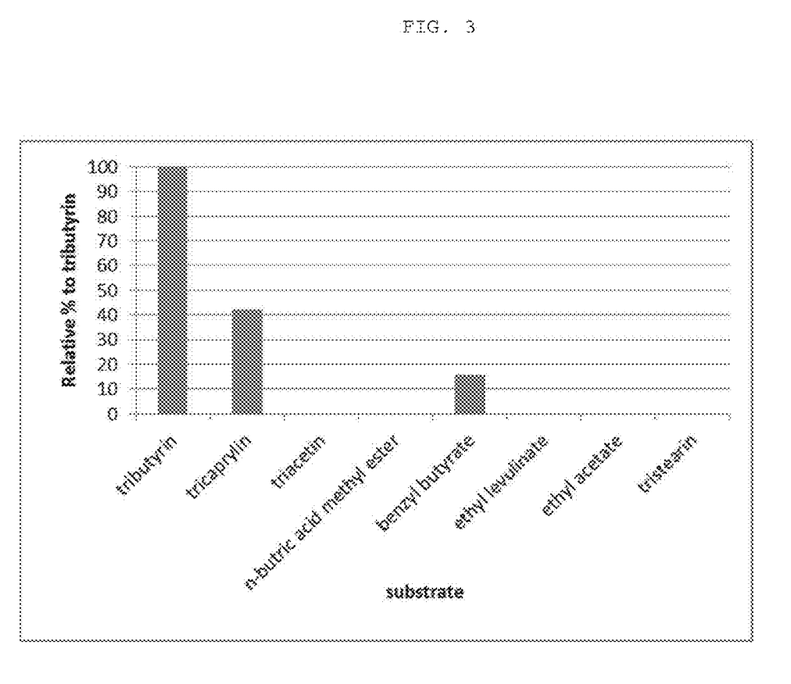
FIG. 3 is a chart depicting various ester substrates used in connection with the present invention.

The rabbit gastric extract was assayed to determine whether lipase activity is present using a standard analytical 'pH stat' laboratory method. The rabbit gastric extract was further assayed with a range of readily available ester substrates, including tributyrin, triaceprylin, triacetin, n-butyric acid methyl ester, benzyl butyrate, ethyl levulinate, ethyl acetate and tristearin. Activity on other triacylglycerol (tricaprylin) and monobutyrate ester (benzylbutyrate) was detected. The results of those assays are depicted in FIG. 3.

Figure 4:
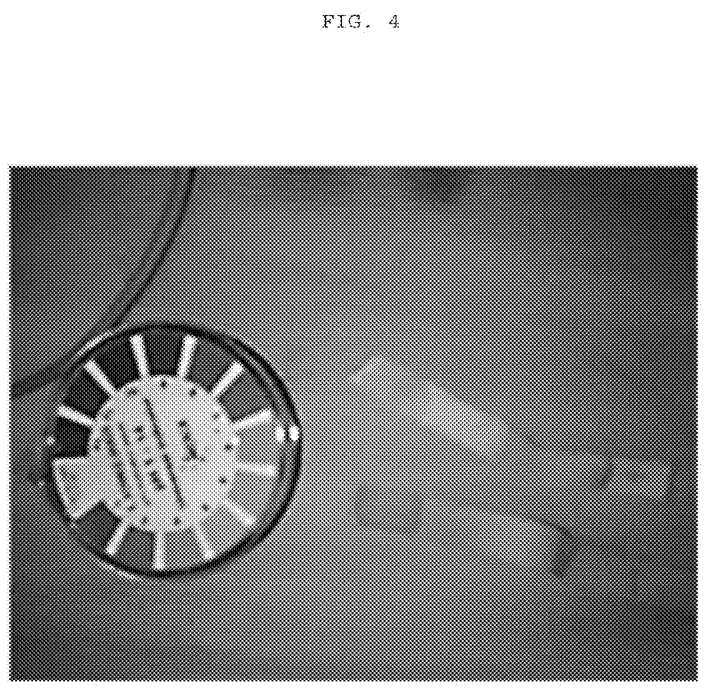
FIG. 4 is a photograph depicting the results of the assay of the present invention wherein the lower strip has a pH=6 and the upper strip a pH=4.

A prototype of the bedside strip was tested using reconstituted rabbit gastric extract which mimics human gastric juice. A control pH strip having no ester substrate was dipped and dried with the pH strip assay mixture (assay mixture comprises of 1 g/L sodium tauroxycholate, 9 g/L sodium chloride and 0.1 g/L bovine serum albumin) and a test pH strip having tributyrin added and suspended at 17 g/L in the assay mixture was dipped and dried. A 10 microliter drop of reconstituted rabbit gastric extract was applied to the left hand of the strip. After 5 seconds, as the results demonstrate in FIG. 4, the lower strip without an ester substrate had a pH of 6, and the upper strip having tributyrin had a of 4. The results confirm that a bedside test for screening the presence of a lipase with an ester substrate results in an overall net decrease of pH because of the release of a carboxylic acid and alcohol product. Consequently, the lowering of the pH with the bedside test of the present invention gives a clear and unequivocal confirmation of the presence of gastric lipase which does not occur in the absence of gastric lipase or its substrate.

EXAMPLE THREE

Figure 5:
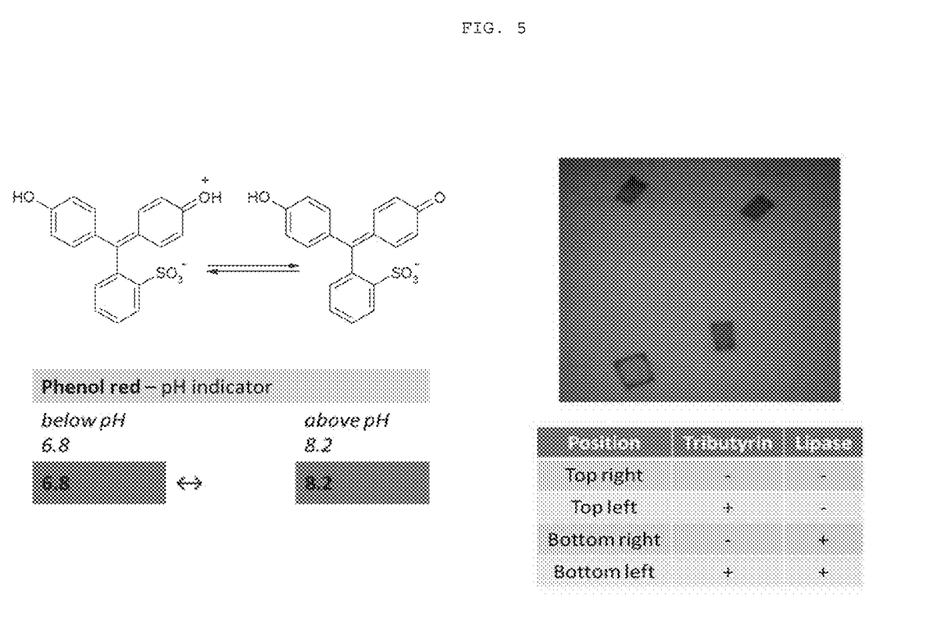
FIG. 5 is a photograph depicting the results of the assay of the present invention using a yes/no test.

A significant aspect of the present invention is providing a point of care test for determining proper placement of a feeding tube which can be readily used in a clinical bedside environment. To make the test easier to read, an alternate pH strip design was tested using yes/no technology similar to home pregnancy test kits. The pH strip was prepared with 0.2% w/v phenol red, 1% w/v tributyrin in methanol. The pH was increased to 9.5 by the addition of sodium hydroxide. The phenol red indictor test shows a color change for a pH below 6.8 (yellow) and no change for a above 8.2 (red). The initial pH before applying the sample is high and thus the phenol red is red in color due to the addition of sodium hydroxide in formulating the strip. Only when the enzyme and substrate are both present is sufficient acid generated in the strip to lower the pH enough to allow the phenol red to convert from a red color to a yellow color. In the absence of enzyme or substrate the acid cannot form and the phenol red remains red. The results are depicted in FIG. 5 and Table 2 below.

TABLE 2

| Position | Tributyrin | Lipase |
| --- | --- | --- |
| Top Right | − | + |
| Top Left | + | − |
| Bottom Right | − | + |
| Bottom Left | + | + |

EXAMPLE FOUR

Figure 6:
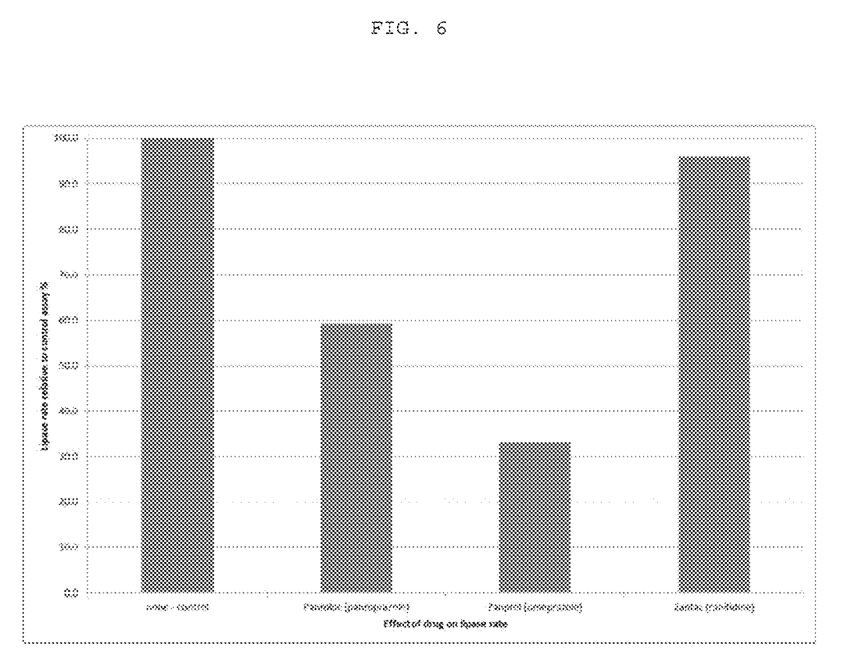
FIG. 6 is a graphical representation showing enzymatic activity is not interfered with in the presence of certain prescription drugs.

As discussed above, one of the current problems with verifying correct placement of a feeding tube based on the pH of an aspirate sample is that prescription drugs will inherently increase the gastric pH of a patient resulting in inaccurate and unreliable diagnosis. To determine whether the present invention is still effective in the presence of prescription drugs, the effect of certain prescription drugs, namely Pantoloc (pantoprazole), Zanprol (omeprazole) and Zantac (rantidine) on lipase activity was tested. The results which are shown in FIG. 6 indicate that enzyme activity is not inhibited by the presence of a drug. For ranitidine there is no discernable decrease in enzyme activity, whereas pantoprazole and omerprazole showed a decrease in enzyme activity. Although enzyme activity decreased, there still remains a detectable amount of enzyme for use with the present invention.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the following claims.

What is claimed is:

1. A method for accurately positioning a medical device in a patient, the method comprising:
   providing a medical device;
   obtaining a body fluid sample from the area of the body where the medical device is positioned;
   providing a pH indicator device impregnated with an enzyme substrate; and,
   screening the body fluid sample with the pH indicator device at a point of care to determine accurate positioning of the medical device based on the catalytic action of an enzyme in the body fluid sample on the enzyme substrate,
   wherein the catalytic action of the enzyme yields a pH less than a pH of a sample without the enzyme using a standard pH test.

2. The method of claim 1, wherein the enzyme is specifically found in the area of the body where the medical device should be positioned.

3. The method of claim 1, wherein the enzyme is a hydrolase.

4. The method of claim 3, wherein the enzyme is a lipase or esterase.

5. The method of claim 3, wherein the enzyme substrate is an ester.

6. The method of claim 1, wherein the method of detecting is non-invasive.

7. The method of claim 1, wherein the enzyme is human gastric lipase (HGL).

8. The method of claim 7, wherein the enzyme substrate is tributyrin, tricaprylin, triacetin, n-butyric acid methyl, benzyl butyrate, ethyl levulinate, ethylacetate or tristearin.

9. The method of claim 1, wherein the medical device is a nasogastric tube, orogastric tube or PEG tube.

10. A method for accurately positioning a medical device in a patient, the method comprising:
    providing a medical device;
    obtaining a body fluid sample from the area of the body where the medical device is positioned;
    providing a pH indicator device impregnated with an ester substrate; and,
    screening the body fluid sample with the pH indicator device at a point of care to determine accurate positioning of the medical device based on the catalytic action of human gastric lipase in the body fluid sample on the ester substrate,
    wherein the catalytic action of human gastric lipase yields a pH less than a pH of a sample without using a standard pH test.

11. The method of claim 1, wherein the pH indicator device is positioned on the medical device.

* * * * *